US00PP09658P

United States Patent [19]

Nies

[11] Patent Number: Plant 9,658

[45] Date of Patent: Oct. 15, 1996

[54] CHERRY TREE 'LARGE RED'

[76] Inventor: Marvin L. Nies, 9296 E. Kettleman, Lodi, Calif. 95240

[21] Appl. No.: 512,696

[22] Filed: Aug. 8, 1995

[51] Int. Cl.[6] ..... A01H 5/00

[52] U.S. Cl. ..... Plt./37

[58] Field of Search ..... Plt./37

*Primary Examiner*—James R. Feyrer

[57] ABSTRACT

A hardy tree from 'Hardy Giant' × 'Berryessa', of medium size and vigor, with spreading, pendulous brances at right angles to the main scaffolds; requires little pruning. Leaves are large, ovate, abruptly acuminate, acutely pointed and have medium coarsely crenate margins. Crops are even from year-to-year with uniform fruit placement on branches and throughout the tree. Blooming is later than 'Ruby', slightly later than 'Garnet', and with 'Bing', at Lodi, Calif. Fruit stem character varies with rootstock. Fruit matures evenly, is uniformly very large, has firm meaty flesh, and evenly ripens to dark red skin, flesh and juice at Lodi on about May 17 for a single pick. Flavor of the semi-free stone fruit is excellent with high but balanced soluble solids and moderate acidity. Eating quality is best.

1 Drawing Sheet

FIELD OF INVENTION

The present variety of cherry tree has been denominated varietally as "Large Red," however, the fruit produced will be marketed under the Trade Mark "LODI". This variety is the outgrowth of a plant breeding program which has been conducted by me on a continuous basis since 1957 in my Experimental orchard near Lodi, County of San Joaquin, Calif. One part of the program has been to develop new and distinct varieties of cherries to be grown commercially in the warmer, lower humidity, lower chilling, earlier production areas, with the tree to have edequate heat tolerance, having fruit that is large, firm, early ripening, resistant to the development of suture, spurs, and doubles; outstanding flavor, non-astringent, high soluble solids with medium acidity. non-browning skin and flesh, adequate disease and insect resistance, wtih a pleasing sugar-acid ratio. The present variety has achieved these objectives with the exception of a tendency to develop spurs on the fruit in hot climates and a tendency to develop surface browning on the skin from leaf rub in windy years; which appears just before harvest when the fruit is pink to light red in color. Shortly thereafter the golden brown color is masked by the dark red pigment to become inconspicuous. The present cherry tree is embraced by Subclass 37, Plants, of the Plant Patent Office Manual Of Classification.

PRIOR VARIETIES

Among the extisting varieties of cherry trees which are known to me are those mentioned herein; to-wit Prunnus mahaleb rootstock (unpatented). Colt rootstock (U.S. Plant Pat. No. 4,059). Starking Hardy Giant (U.S. Plant Pat. No. 764, Garnet (U.S. Plant Pat. No. 4,431), Ruby (U.S. Plant Pat. No. 4,436), Bing (unpatented), and Berryessa (an unpatented white variety developed by the University of California, Davis, Calif.

ORIGIN OF THE VARIETY

The present variety, denominated varietally as "Large Red," relates to a distinct variety of cherry tree originated by me, the fruit of which was first observed by me in 1968 in the seedling block of my experimental orchard in a cultivated area at the Marvin L. Nies Ranch near Lodi, County of San Joaquin, Calif., and was initiated in 1963 by crossing the selected seed parent Hardy Giant with the selected pollen parent Berryessa, which resulted in seeds from the seed parent, which when germinated and grown, produced some seedlings, one of which was the present variety; the location of which in the seedling block was recorded in my Breeding Records as Seedling MR 4-44, and which when grown to maturity, evidenced novel and distinctive characteristics, and I therefore selected it for asexual reproductions preparatory to patenting and ultimate commercial growing thereof.

ASEXUAL REPRODUCTION OF THE VARIETY

Subsequent to the origination of the present variety of cherry tree I asexually reproduced the selection on Prunus mahaleb rootstock and at a later date on Colt rootstock in my experimental orchard near Lodi, County of San Joaquin, Calif., by budding and grafting, and such reproduction of plant and fruit characteristics were true to the original plant at maturity in all respects.

SUMMARY OF VARIETY

My first observation of the fruit of this variety was made in 1968 in my experimental orchard seedling block in Lodi, San Joaquin County, Calif. What set the present variety apart from the sister seedlings was that it was very precocious, even cropping without a tendency to overcrop, even distribution of the fruit throughout the tree, very large fruit size, medium viror, a desirable weeping tree habit, unusually high soluble solids when pin speckled ripe, with low to medium acidity when mature, even maturity when shipping ripe, flesh of the fruit being quite firm and meaty (slightly softer than Bing, the industry standard for firmness), semi-free, long fruit stems, light red flesh and juice when red ripe, dark red flesh and juice when fully mature, resistant to suture, resistant to cracking in wet weather, and excellent sugar-acid ratio with excellent flavor and eating qualities. The medium low acidity and high soluble solids make this variety an excellent candidate for European and Pacific Rim exports. The tree has a naturally self shaping open tree habit, with right angled lateral branches originating from the upright branches, having many small twigs two years or older that are pendulous and a tree that requires little if any pruning up to the tenth year. The variety is generally picking ripe eight (8) days after Ruby, three (3) days after Garnet and thread days ahead of Bing. Since thinning of fruit in cherries does not increase fruit size because of the generally short Fruit Development Period (FDP), "what you see is what you get". Consequently growers traditionally attempt to control the crop level primarily by pruning and varying the amount if pollinization in the orchard because there two factors are the most obvious and easy to implement. Until recently, the number of commercial varieties that were acceptable at best from a production and quality standpoint were quite limited. It is obvious that obtaining optimum (normal) crop levels that result in large, firm, high quality fruit from year to year, is very difficult if not impossible to attain. The genetic mechanisms that regulate crop level in the present commercial varieties appear to be inadequate to respond to the highly variable, uncontrollable climatic conditions. Whatever horticultural manipulation a grower may engage in to regulate crop levels or may not be successful and may not coincide with the trees response to the variables on any one year. Heavy crops create soft fruit — low in soluble solids, less flavor, more susceptibility to fruit damage (pitting) from the packing operation resulting in a product that is of poor quality and that has very poor shelf life on the retail level with the inevitable demand by the trade for a price adjustments. Lighter yields can result in excellent quality, firm, high soluble solids, flavorful fruit, however, cash returns may suffer due to lack of volume. The present variety is genetically very unusual in producing relatively even crop levels from year to year. Some of the more easily recognized variables that contribute to the ultimate crop level on any one year are weather conditions throughout growing season before the next harvest, cultural practices (primarily pruning and irrigation), the number of pollinizer trees in relation to the main production variety and number of hours of optimum pollinization during bloom. This variety's natural disposition to adapt to these varying conditions by producing a relatively normal crop load on any given year, with consistently excellent shipping quality are very important considerations when selecting a variety for commercial production. The FDP for each individual fruit in cherries is quite consistent from year to year and consequently late straggle bloom results in uneven maturity of the fruit at harvest time making it necessary to color pick. Color picking is a difficult to control farming operation and significantly increases the cost of harvesting and packing with the end result being a large increase in the cost of the packed box. In addition, irregular maturity of the fruit makes for a less desirable checkerboard appearing packed box which is not in as much demand in the marketplace. There are also significant losses in cull green fruit that is not marketable, a loss not only of the value of the fruit eliminated but also the cost of harvesting and handling of the fruit. When considering all of the above enumerated qualities this selection is prime candidate for the ultimate commercial growing thereof.

DRAWING

The accompanying photograph exhibits clusters of whole fruits positioned to display the characteristics of the skin color, stem length and fruit form; on a representative branch with leaves and also seven (7) detached fruits with one sectioned fruit showing a longitudinal (ventral) cross-section, displaying the color and texture of the flesh and also the shape, color and ventral texture of the stone.

POMOLOGICAL CHARACTERISTICS

The botanical details of this new and distinct variety of cherry tree with color definitions (except those in common color terms) referenced to The Wilson Colour Chart I and II, published by The British Colour Council— Horticultural Color Chart (1938) are as follows:

Tree:

*Size.*—Semi-dwarf on *Prunus mahaleb* and Colt rootstocks.

*Vigor.*—Medium.

*Growth.*—Open. Spreading-pendulous

*Density.*—Open.

*Form.*—Bushy, Rounded.

*Hardiness.*—Hardy

*Production.*—Even crop levels from year to year, very little tendency to overcrop. Even distribution of the fruit throughout the tree.

Trunk:

*Size.*—Medium.

*Texture.*—Medium.

Branches:

*Size.*—Medium.

*Texture.*—Medium.

*Color.*—Orange brown on younger growth. Gray dull on older wood.

*Lenticles.*—Pronounced. Medium size. Number: Very numerous near base of first years shoot being rounded elliptical in shape and oriented perpendicular to the axis of the branch.

Leaves:

*Size.*—Large. Average length (25 leaves) 16.2 cm. Average width (25 leaves) 7.7 cm.

*Veination.*—Large vein centrally oriented from base of blade to apex. Lateral veins-almost without exception alternate-oblique towards apex of blade-extending from main central vein to near the edge of blade forming a looped configuration.

*Ratio.*—Length/width of blade—0.475 (average of 25 Leaves) This ratio is quite consistent over a wide range of leaf sizes.

*Form.*—Ovate. Abruptly acuminate. Acutely pointed.

*Thickness.*—Thick.

*Color.*—Top of leaf-dark green. Bottom of leaf-light green.

*Texture.*—Smooth.

*Margin.*—Coarsely serrate-crenate. Occasional a small sharp tooth before and attached to the base of a large tooth.

*Petiole.*—Quite long. Ratio of petriole length/length of blade —0.35 (Average 25 leaves. Very lightly pigmented upper side Dahilia Purple(P 3/31)—No pigment underside.

*Glands.*—Color — Light red. Reiniform. Compressed. Number on petiole — Predominately two (2), many times one(1), occasionally none, rarely more than two(2). There seems to be a correlation between leaf size and number of glands, the larger leaves generally having two (2) with the smaller leaves have one (1) and occasionally none. Size — A great deal of variation in size from almost inconspicuous on some leaves to medium large on larger leaves. Generally alternate-opposite but occasionally separated by varying distances.

*Stipules.*—Two (2)- one (1) on each side of petiole on younger leaves.

Flower buds:

*Hardiness.*—Hardy.

*Size.*—Medium.

*Length.*—Medium.

*Form.*—Conic-plump.

Flowers:

*Date of bloom.*—Mar. 16, 1994.

*Petals.*—Size: Medium large-length 15.5–18.0 mm. Width — 14.0–16.0 mm. Color—Pure white, occasional pinkish tinge on edge of petal Mostly notched at the apex.

*Filament length.*—1 cm.

*Stigma length.*—1.5 cm

*Hypanthium.*—Medium-five (5) sepals-strongly reflexed on older flowers. Very light pigmentation. Facing sun— Chrysanthemum crimson 824/3.

*Blooming period.*—Compact-no straggle bloom-resulting in even maturity.

*No. of flowers per bud.*—Two to three (2–3).

Fruit:

*Maturity when described.*—Eating ripe— May 18, 1994.

*Date of first picking.*—May 18, 1994. All fruit on individual trees picked at one time.

*Size.*—Very uniform. Large. Widest average diameter-transverse plane — 2.6 cm. suture plane — 2.2 cm. Maximum size 75/64"(9Row).

*Form.*—Globose. Uniform. Symmetrical transversely to the suture plane.

*Suture.*—Generally none.

*Ventral surface.*—Rounded strongly from base to apex.

*Stem cavity.*—Flaring and circular. Medium depth.

*Color.*—Dark red when fully mature with uniform color over the total surface of the fruit, pronounced speckling on immature fruit near full red maturity.

*Base.*—Rounded.

*Apex.*—Rounded.

*Pistil point.*—Apical. An inconspicuous brown abscission point.

*Ripening span.*—Very even ripening. One picking.

Skin

*Thickness.*—Medium.

*Texture.*—Medium.

*Tenacity.*—Tenacious to flesh.

*Tendency to crack.*—None in dry weather. Crack resistant with normal crop levels, being considerable more resistant than Bing and Garnet to cracking in the record wet weather conditions of 1995.

*Color.*—Currant Red (8/21)—mature fruit-picking ripe.

*Down.*—Wanting.

*Surface.*—Shiny.

Flesh:

*Color.*—Red (Currant Red 821/2)—fully mature fruit.

*Surface of pit cavity.*—Red (Currant Red 821).

*Amygdalin.*—Wanting.

*Texture.*—Firm-fine-meaty.

*Aroma.*—Wanting.

*Fibres.*—Few-fine.

*Ripens.*—Very evenly.

*Flavor.*—Excellent at full maturity.

*Eating quality.*—The best. High soluble solids. Low to moderate acidity. Excellent sugar/acid ratio.

*Tendency to crack.*—Resistant to cracking in wet weather None in dryweather.

Stone

*type.*—Semi-free. Flesh adheres slightly to winged portion of ventral edge of stone.

*Size.*—Medium large. Average length—1.2 cm. Average width —8.0-mm. Average breadth 8.5 mm.

*Form.*—Globose

*Base.*—Ventral side fairly straight-slightly oblique. Dorsal side — rounded-oblique to a point.

*Hilum.*—Long. Narrow. Oblong.

*Apex.*—Pointed.

*Sides.*'Equal. Symmetrical.

*Surface.*—Smooth from dorsal edge to ventral edge with the exception of wide ridged furrows extending from hilum ¼ of the distance to apex.

*Ridges.*—Jagged

*Ventral edge.*—Thick. Six (6 mm) wide at the center of the stone. Elliptical. Three(3) prominent ridges extending form hilum to apex. One central and one on each side to form an elliptical configuration. Lateral ridges curve away from central ridge (3 mm) at the mid-point of the stone.

*Dorsal edge.*—Narrow ridge.

*Color.*—Egyptian buff (407/1).

*Form.*—Oval. flattened of ventral side. Rounded on dorsal side from hilum to apex.

*Taste.*—Seed very bitter.

*Viability.*—Very low.

*Amygdalin.*—Abundant.

Use:

*Market.*—Dessert — Shipping.

Keeping quality: Excellent.

Resistance to insects and diseases: No unusual susceptibilities note.

Shipping quality: Good — both local and long distance.

Variance in botanical details: Although the new variety of cherry possesses the described characteristics under the ecological condiutions at Lodi, Calif., in the Northern part of the San Joaquin Valley, it is to be expected some variations in some of there pomological characteristics may occur when grown in areas with different climatic conditions, different soil types, and/or varying cultural practices.

I claim:

1. A new and distinct variety of cherry tree, substantially as illusrated and described, being of medium vigor, tending to be dwarfing and quite pendulous, lateral branches at right angles to the main branches, tree habit very open, spreading, self shaping, requiring almost no pruning up to the tenth year, numerous pendulous second year small twigs on older trees, right angled lateral twigs emanatig from large branches, the fruit being very large and uniform in size the length of the branch, fruit being almost round in the transverse cross section and slightly less round in the suture plane, crop very evenly distributed throughout the tree, having high soluble solids with very moderate acidity even on green speckled fruit, red spots on pinkish green to light red background which blend in when the fruit colors to a dark solid red, having a fairly long fruit stem of medium thickness and with fruit that is physically easy to remove from the tree by pickers; when compared with Garnet, a more precocious tree, fruit that is a slightly less firm, lighter red flesh and juice at maturity. picking ripe two to three (2–3) days later, having a similar chilling requirement, being much more precocious, bearing earlier on small trees and having more crack resistance in wet weather; when compared with Bing, ripens three (3) days earlier, is slightly less firm, has larger size with equivalent crop levels, longer stems, considerably more crack resistance in wet weather, higher soluble solids and very much less acidity at the same stage of ripening, very much larger size with the same crop load, rounded transverse cross section as opposed to the flattened ventral surface of the Bing fruit, rounded apex as opposed to a more pointed fruit of Bing, with less spurs and almost no suture in the hotter Central Valley of Northern California.

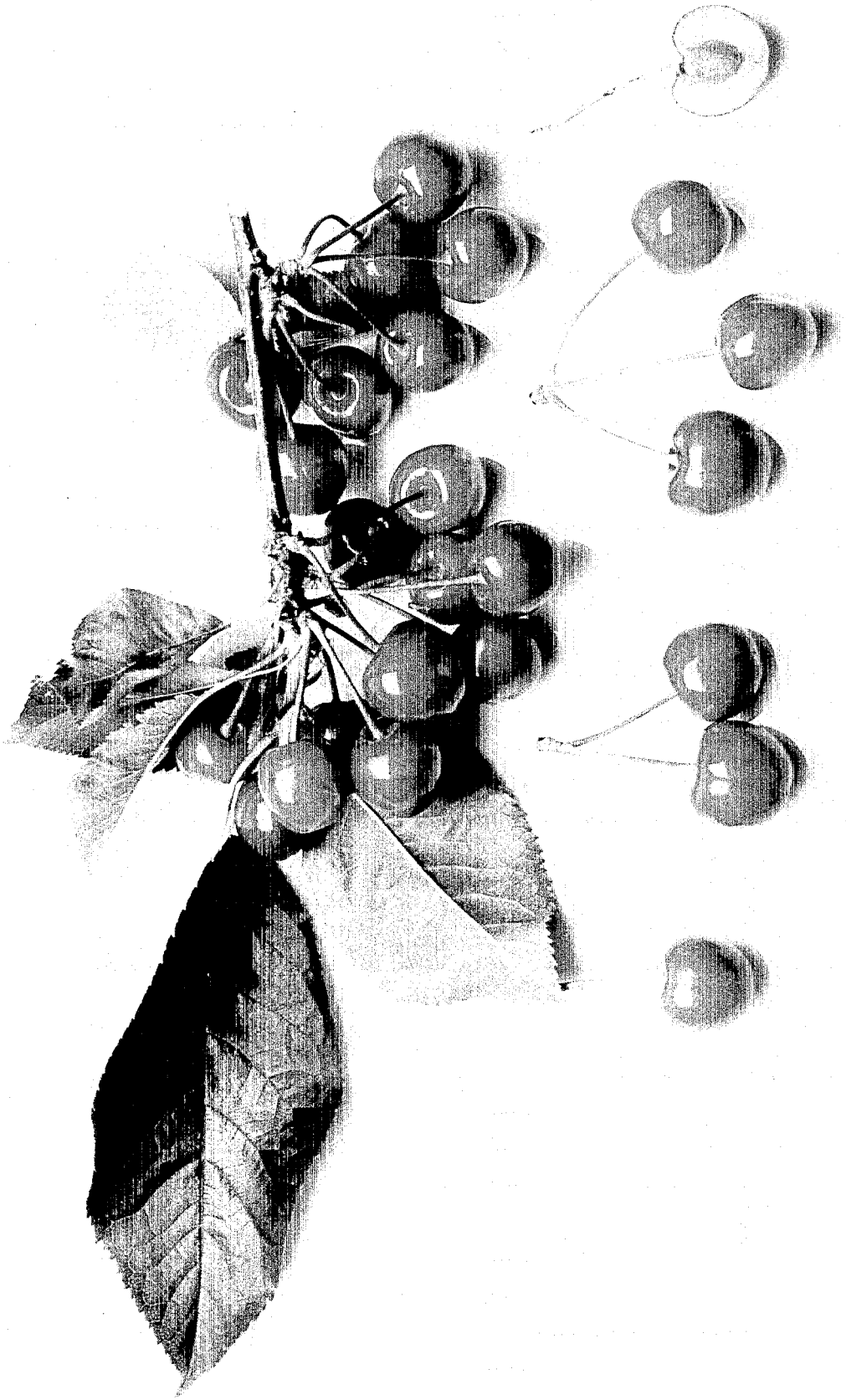

* * * * *